United States Patent [19]

Simon et al.

[11] Patent Number: 5,280,031

[45] Date of Patent: Jan. 18, 1994

[54] CYCLIC AZAALIPHATIC COMPOUNDS WITH A NITROXY FUNCTION, PROCESSES FOR THE PREPARATION THEREOF AND PHARMACEUTICAL COMPOSITIONS CONTAINING THEM

[75] Inventors: Herbert Simon, Lampertheim; Helmut Michel; Michael Schultz, both of Mannheim; Wolfgang Bartsch, Viernheim, all of Fed. Rep. of Germany

[73] Assignee: Boehringer Mannheim GmbH, Mannheim, Fed. Rep. of Germany

[21] Appl. No.: 699,832

[22] Filed: May 14, 1991

Related U.S. Application Data

[62] Division of Ser. No. 424,451, Oct. 20, 1989, Pat. No. 5,030,641.

[30] Foreign Application Priority Data

Oct. 22, 1988 [DE] Fed. Rep. of Germany ....... 3836084

[51] Int. Cl.$^5$ .................. A61K 31/445; C07D 211/28; C07D 207/08
[52] U.S. Cl. .................................. 514/331; 514/330; 514/408; 514/423; 514/428; 546/242; 546/245; 546/246; 548/517; 548/538; 548/566; 548/570
[58] Field of Search ........................ 546/242, 245, 246; 548/570, 517, 538, 566; 514/345, 330, 428, 423, 331, 408, 315

[56] References Cited

U.S. PATENT DOCUMENTS

| | | | |
|---|---|---|---|
| 3,869,463 | 3/1975 | Archibald | 546/201 |
| 4,405,334 | 9/1983 | Seemuth | 546/242 |
| 4,801,596 | 1/1989 | Simon | 546/220 |

FOREIGN PATENT DOCUMENTS 0280951 3/1975 European Pat. Off. .
0101093 2/1984 European Pat. Off. .

OTHER PUBLICATIONS

*Chemical Abstracts*, vol. 106, No. 186566r (1988), pp. 688–689.
*Physical Organic Chemistry*, vol. 97, 109228j (1982), p. 539.
*Chemical Abstracts*, vol. 103, 141568y (1985), p. 686.
*Chemical Abstracts*, vol. 104, 88398k (1986), p. 644.

Primary Examiner—C. Warren Ivy
Assistant Examiner—Celia Chang
Attorney, Agent, or Firm—Nikaido, Marmelstein, Murray & Oram

[57] ABSTRACT

The present invention provides anti-angina pharmaceutical compositions containing at least one compound of the formula:

$$R-N\underset{\diagdown}{\overset{(CH_2)_n}{\diagup}}\boxed{\phantom{XX}}-A-B-ONO_2 \qquad (I)$$

wherein n is 1 or 2, R is a hydrogen atom or an H—($C_1$-$C_8$)-alkylene, hydroxy-($C_1$-$C_8$)-alkylene, $R^1R^2N$—($C_1$-$C_8$)-alkylene, $R^1R^2N$—($C_1$-$C_8$)-alkylene-CO—, $R^1R^2N$—CO—$NR^3$—($C_1$-$C_8$)-alkylene or $R^1R^2N$—CO— radical, A is a valency bond or an —$NR^4$—CO— or —CO—$NR^4$— radical, $R^4$ is a hydrogen atom or a straight-chained or branched, saturated or unsaturated or cyclic alkyl radical containing up to 6 carbon atoms and B is a valency bond or a straight-chained or branched alkylene chain containing up to 8 carbon atoms, in which a —$CH_2$— group can be replaced by a cycloalkylene radical containing 3 to 7 carbon atoms.

19 Claims, No Drawings

CYCLIC AZAALIPHATIC COMPOUNDS WITH A NITROXY FUNCTION, PROCESSES FOR THE PREPARATION THEREOF AND PHARMACEUTICAL COMPOSITIONS CONTAINING THEM

This is a division, of application Ser. No. 424,451 filed Oct. 20, 1989, now U.S. Pat. No. 5,030,641.

The present invention is concerned with cyclic azaaliphatic compounds with a nitroxy function, with processes for the preparation thereof and with pharmaceutical compositions containing them.

The azaaliphatic compounds according to the present invention are compounds of the general formula:

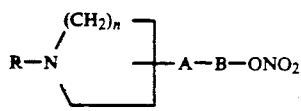
(I)

wherein n is 1 or 2, R is a hydrogen atom or an H—($C_1$–$C_8$)-alkylene, hydroxy-($C_1$–$C_8$)-alkylene, $R^1R^2N$—($C_1$–$C_8$)-alkylene, $R^1R^2N$—($C_1$–$C_8$)-alkylene-CO—, $R^1R^2N$—CO—$NR^3$—($C_1$–$C_8$)-alkylene or $R^1R^2N$—CO— radical, $R^1$ is a hydrogen atom or a straight-chained or branched saturated or unsaturated or cyclic alkyl radical containing 1 to 6 carbon atoms, $R^2$ is a hydrogen atom or a straight-chained or branched, saturated or unsaturated or cyclic alkyl radical containing 1 to 6 carbon atoms or $R^2$, together with a —$CH_2$— group of the neighbouring $C_1$–$C_8$-alkyl radical and the nitrogen atom can bridge a heteroaliphatic ring containing 2 to 6 carbon atoms, $R^3$ is a hydrogen atom or a straight-chained or branched, saturated or unsaturated or cyclic alkyl radical containing 1 to 6 carbon atoms, A is a valency bond or an —$NR^4$—CO— or —CO—$NR^4$— radical, in which $R^4$ is a hydrogen atom or a straight-chained or branched, saturated or unsaturated or cyclic alkyl radical containing 1 to 6 carbon atoms and B is a valency bond or a straight-chained or branched alkylene chain containing 1 to 8 carbon atoms in which a —$CH_2$— group can be replaced by a cycloalkylene radical containing 3 to 7 carbon atoms, with the proviso that R cannot be an $R^1R^2N$—($C_1$–$C_8$)-alkylene-CO— radical in which $R^1$ and $R^2$ are both hydrogen atoms and with the proviso that R cannot be an H—($C_1$–$C_8$)alkyl radical when A and B are both valency bonds and n is 2; as well as the optically-active forms and physiologically acceptable salts thereof.

The compounds of general formula (I) according to the present invention possess valuable properties. They bring about a reduction of the oxygen requirement of the heart, an increase of the blood flow and a lowering of the blood pressure. Surprisingly, we have also found that the compounds according to the present invention display a nitrate-like action of especially long duration. Therefore, they are suitable for the prophylaxis and/or treatment of heart and circulatory diseases, for example angina pectoris.

Similar compounds of general formula (I), in which R is an amino-($C_1$–$C_8$)alkylenecarbonyl radical are already known from European Patent Specification No. A-0,280,951. They are there described as compounds of general formula (IV) and are merely intermediates for the preparation of aryloxyaminopropanol derivatives. A pharmacological action of these compounds was hitherto not known.

Azaaliphatic compounds in which n is 2 (piperidine derivatives), wherein A and B both represent valency bonds and R is a $C_1$–$C_{20}$-alkyl radical are known from European Patent Specification No. A-0,101,093 (Ethyl Corporation) as additives for diesel fuels, especially the compounds 1-methyl-3-nitroxypiperidine and 1-methyl-4-nitroxypiperidine. Furthermore, the compound 1-methyl-4-nitroxypiperidine is described in U.S. Pat. No. 4,405,334 (Chemical Abstracts, 100, P 9842 S).

For the compounds known from the prior art, hitherto no pharmacological action has been described so that the present invention also provides pharmaceutical compositions which can contain not only these known compounds but also the new compounds of general formula (I).

R can be a hydrogen atom or an H—($C_1$–$C_8$)-alkylene, hydroxy-($C_1$–$C_8$)-alkylene, $R^1R^2N$—($C_1$–$C_8$)-alkylene, $R^1R^2N$—($C_1$–$C_8$)-alkylene-CO—, $R^1R^2N$—CO— or $R^1R^2N$—CO—$NR^3$—($C_1$–$C_8$)-alkylene radical. ($C_1$–$C_8$)-alkylene can thereby be a straight-chained, branched or cyclic alkylene chain, preferably methylene, ethylene, trimethylene, tetramethylene, pentamethylene, as well as hexamethylene, heptamethylene or octamethylene radical. ($C_1$–$C_8$)-alkylene can also be branched and contain 2 to 8 and preferably 2 to 5 carbon atoms. There are preferred, for example, methylmethylene, 1-methylethylene, dimethylmethylene, 1,1-dimethylethylene, 1,1-dimethyltrimethylene, 1-methyltrimethylene, as well as, for example, 2,2-dimethylethylene, 1-ethylmethylene, 1,1-dimethyltetramethylene, 1,2-dimethyltrimethylene, 2,2-dimethyltrimethylene, 3,3-dimethyltrimethylene, 1,1-dimethylpentamethylene, 1,1-dimethylhexamethylene or 1-methyltetramethylene radicals.

The ($C_1$–$C_8$)-alkylene radical can also be cyclic and contain 3 to 8 and preferably 6 carbon atoms. There is preferred the 1,2-, 1,3- or 1,4-cyclohexylene radical, wherein the position of the substituents can be cis or trans. Furthermore, there can be used, for example, the methylene-1,2-, -1,3- or 1,4-cyclohexylene radical, the methylene-1,2-, -1,3- or -1,4-cyclohexylenemethylene radical or the ethylene-1,2-, -1,3-or -1,4-cyclohexylene radical, the configuration of the cycloalkylene radical being in each case cis or trans. Further ($C_1$–$C_8$)alkylene chains include, for example, the 1,2-cyclopropylene radical, the methylene-1,2-cyclopropylene radical, the tetramethylene-1,2-cyclopropylene radical, the methylene-1,2-cyclopropylenemethylene radical, the methylene-1,2-cyclopropyleneethylene radical, the 1,2- or 1,3-cyclobutylene radical, the methylene-1,2- or -1,3-cyclobutylene radical, the tetramethylene-1,2- or -1,3-cyclobutylene group, the methylene-1,2- or -1,3-cyclobutylenemethylene radical, the methylene-1,2- or -1,3-cyclobutyleneethylene radical, the 1,2- or 1,3-cyclopentylene radical, the methylene-1,2- or 1,3-cyclopentylene radical, the methylene-1,2- or -1,3-cyclopentylenemethylene radical, the methylene-1,2- or -1,3-cyclopentyleneethylene radical, the 1,2-, 1,3- or 1,4-cycloheptylene radical, the methylene-1,2-, -1,3-or -1,4-cycloheptylene radical, the configuration of the cycloalkylene radical being in each case cis or trans.

$R^1$ can be a hydrogen atom or a straight-chained, branched or cyclic alkyl chain containing up to 6 carbon atoms, preferably methyl, ethyl, n-propyl, isopropyl, n-butyl, n-pentyl, cyclopropyl, cyclopentyl and cyclohexyl, as well as, for example, isobutyl, tert.-butyl, 2-pentyl, 2-hexyl and cyclobutyl.

$R^2$ can be a hydrogen atom or a straight-chained, branched or cyclic alkyl chain containing up to 6 carbon atoms, preferably methyl, ethyl, n-propyl, isopropyl, n-butyl, n-pentyl, n-hexyl, cyclopentyl or cyclohexyl, as well as, for example, 2-butyl, isobutyl, 2-pentyl, 2-hexyl or cyclopropyl. In addition, $R^2$, together with a —($CH_2$)— group of the ($C_1$-$C_8$)-alkylene radical and the neighbouring nitrogen atom, can bridge a heteroaliphatic ring containing 2 to 6 carbon atoms. Examples therefor include the aziridine ring, the azetidine ring, the pyrrolidine ring, the piperidine ring and perhydroazepine ring.

$R^3$ can be a hydrogen atom or a straight-chained, branched or cyclic alkyl chain containing up to 6 carbon atoms, preferably methyl, ethyl, n-propyl, isopropyl, n-butyl, n-pentyl, cyclopropyl, cyclopentyl and cyclohexyl, as well as, for example, isobutyl, 2-butyl, 2-pentyl or 2-hexyl.

When n is 1, the A—B—$ONO_2$ radical can be in the 2-or 3-position of the pyrrolidine ring but preferably in the 3-position and, when n is 2, in the 2-, 3- or 4-position of the piperidine ring, the 4-position being preferred.

$R^4$ can be a hydrogen atom or a straight-chained, branched or cyclic alkyl chain containing up to 6 carbon atoms, for example methyl, ethyl, n-propyl, isopropyl, n-butyl, n-pentyl, cyclopropyl, cyclopentyl and cyclohexyl.

B can be a valency bond or a straight-chained or branched alkylene chain containing up to 8 carbon atoms, preferably 2 to 6 carbon atoms, and is preferably ethylene, 1-methylethylene, 2-methylethylene, trimethylene, 1-methyltrimethylene, 3-methyltrimethylene, tetramethylene, pentamethylene, 1-methyltetramethylene, 1-ethyltrimethylene, hexamethylene, 1-methylpentamethylene, 1-ethyltetramethylene, 1-n-propyltrimethylene, 1,1-dimethylethylene, as well as, for example, dimethylmethylene, 1,1-dimethyltrimethylene, 2,2-dimethyltrimethylene, 2,2-dimethyltetramethylene or 1,1-dimethylhexamethylene.

When a —($CH_2$)— group of the chain B is replaced by a cycloalkylene radical, then a 1,2-, 1,3- or 1,4-cyclohexylene radical is preferred, the configuration of the cyclohexylene radical being in each case cis or trans.

Preferred in the meaning of the present invention are those compounds in which R is a hydrogen atom, an H—($C_1$-$C_3$)alkylene radical, for example methyl, ethyl, n-propyl or isopropyl, an HO—($C_1$-$C_3$)-alkylene radical, for example 2-hydroxypropyl, an $R^1R^2N$—($C_1$-$C_3$)-alkylene radical, for example aminoethylene or aminopropylene, an $R^1R^2N$—($C_1$-$C_5$)-alkylenecarbonyl radical, for example aminomethylcarbonyl, dimethylaminomethylcarbonyl, (2-amino-1-methyl)-ethylcarbonyl, 2-aminoethylcarbonyl, 2-(N,N-dimethylamino)-ethylcarbonyl, (3-amino-3-methyl)-butylcarbonyl, 1-aminoethylcarbonyl or (2-amino-2-methyl)-propylcarbonyl, an $R^1R^2N$—CO—$NR^3$—($C_1$-$C_3$)-alkylene radical, for example aminocarbonylaminoethyl, or an $R^1R^2N$—CO— radical, for example isopropylaminocarbonyl or aminocarbonyl, $R^1$ is a hydrogen atom or a straight-chained or branched $C_1$-$C_3$-alkyl radical, for example methyl, ethyl or isopropyl, $R^2$ is a hydrogen atom or a straight-chained $C_1$-$C_3$-alkyl radical, for example methyl or ethyl and $R^2$, together with a —$CH_2$— group of the neighbouring alkylene radical and the nitrogen atom, form a piperidine ring, $R^3$ is a hydrogen atom, A is a valency bond or an —NH—CO— or —CO—NH— group and B is a valency bond, a straight-chained or branched $C_1$-$C_5$-alkylene radical, for example methylene, ethylene, trimethylene or 1,1-dimethylethylene or a 1,4-cyclohexylene radical.

The compounds according to the present invention are usually administered in amounts of from 20 to 500 mg. per day, referred to a body weight of 75 kg. It is preferred to administer 1 or 2 tablets with a content of active material of from 10 to 300 mg. once or twice a day. The tablets can also be retarded, whereby 1 or 2 tablets with 20 to 600 mg. of active material have to be given once per day. The active material can also be administered by injection 1 to 8 times a day or by continuous infusion, in which case amounts of from 5 to 200 mg. per day normally suffice.

The compounds of general formula (I) according to the present invention can be prepared, for example, in the following way:

1) a compound of the general formula:

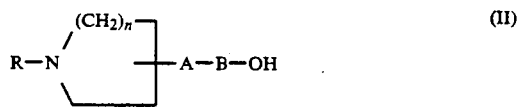

(II)

in which A, B, R and n have the above-given meanings, is subjected to a nitrate ester forming reaction, or 2.1) when A is an —$NR^4$—CO— radical, a compound of the general formula:

(III)

in which n, R and $R^4$ have the above-given meanings, is reacted with a compound of the general formula:

$$Z-CO-B-ONO_2 \qquad (IV)$$

in which n, R, $R^4$ and B have the above-given meanings and Z is a nucleofuge group, or 2.2) when A is a —CO—$NR^4$ radical, a compound of the general formula:

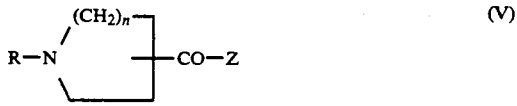

(V)

in which n, R and Z have the above-given meanings, is reacted with a compound of the general formula:

$$HNR^4-B-ONO_2 \qquad (VI)$$

in which B and $R^4$ have the above-given meanings, or 2.3) when R is not a hydrogen atom, a compound of the general formula:

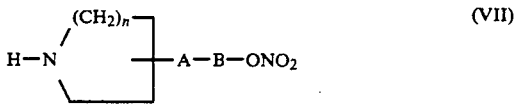

(VII)

in which n, A and B have the above-given meanings, is reacted with a compound of the general formula:

R—Z  (VIII)

in which R and Z have the above-given meanings, or 2.4) when R is an $R^1R^2N$—CO— radical, a compound of general formula (VII) is reacted with an isocyanate of the general formula $R^2$—NCO, in which $R^2$ has the above-given meaning, or with a haloformic acid derivative of the general formula $R^2$—NH—CO—Hal, in which $R^2$ has the above-given meaning and Hal is chlorine or bromine, or 2.5) when R is an $HR^2N$—CO—$NR^3$—($C_1$-$C_8$)-alkylene radical, a compound of the general formula:

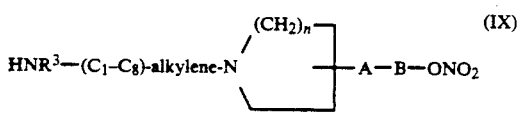
$HNR^3$—($C_1$-$C_8$)-alkylene-N$\diagup^{(CH_2)_n}_{\diagdown}$—A—B—ONO$_2$  (IX)

in which n, $R^3$, A and B have the above-given meanings, is reacted with an isocyanate of the general formula $R^2$—NCO, in which $R^2$ has the above-given meaning, or with a haloformic acid derivative of the general formula $R^2$—NH—CO—Hal, in which $R^2$ and Hal have the above-given meanings.

The compounds of general formula (II), in which R is not an amino-($C_1$-$C_8$)alkylenecarbonyl radical, are new. When R is an amino-($C_1$-$C_8$)-alkylenecarbonyl radical, then these compounds are already known from European Patent Specification No. A-0,280,951 (see general formula (XIII) therein).

Therefore, the present invention also provides new compounds, which can be used as intermediates, of the general formula:

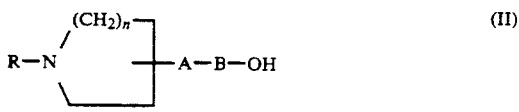
R—N$\diagup^{(CH_2)_n}_{\diagdown}$—A—B—OH  (II)

wherein n is 1 or 2, R is a hydrogen atom or a H—($C_1$-$C_8$)-alkylene, hydroxy-($C_1$-$C_8$)-alkylene, $R^1R^2N$—($C_1$-$C_8$)-alkylene, $R^1R^2N$—($C_1$-$C_8$)-alkylene-CO—, $R^1R^2N$—CO—$NR^3$—($C_1$-$C_8$)-alkylene-or $R^1R^2N$—CO— radical, $R^1$ is a hydrogen atom or a straight-chained or branched, saturated or unsaturated or cyclic alkyl radical containing up to 6 carbon atoms, $R^2$ is a hydrogen atom or a straight-chained or branched, saturated or unsaturated or cyclic alkyl radical containing up to 6 carbon atoms or $R^2$, together with a —($CH_2$)— group of the neighbouring ($C_1$-$C_8$)-alkyl radical and the nitrogen atom, bridge a heteroaliphatic ring containing 2 to 6 carbon atoms, $R^3$ is a hydrogen atom or a straight-chained or branched, saturated or unsaturated or cyclic alkyl radical containing up to 6 carbon atoms, A is a valency bond or an —$NR^4$—CO— or —CO—$NR^4$— radical, in which $R^4$ is a hydrogen atom or a straight-chained or branched, saturated or unsaturated or cyclic alkyl radical containing up to 6 carbon atoms, B is a valency bond or a straight-chained or branched alkylene chain containing up to 8 carbon atoms, in which a —$CH_2$— group can be replaced by a cycloalkylene radical containing 3 to 7 carbon atoms, with the proviso that R cannot be an $R^1R^2N$—($C_1$-$C_8$)-alkylene-CO— radical in which $R^1$ and $R^2$ are both hydrogen atoms and with the proviso that R is not a hydrogen atom or an H—($C_1$-$C_8$)-alkylene radical when A is a valency bond and B is a valency bond or an alkylene chain containing up to 2 carbon atoms; as well as the optically-active forms thereof.

Compounds of general formula (II), in which R is an $R^1R^2N$—($C_1$-$C_8$)-alkylene-CO— radical are known from European Patent Specification No. A-0,280,951. Compounds in which R is a hydrogen atom or an H—($C_1$-$C_8$)-alkylene radical, A is a valency bond and B is a valency bond or an alkylene radical containing up to 2 carbon atoms are described in Chem. Abs., 97, (13), 109228j/1982; Chem. Abs., 103 (17), 141568y/1985; Chem. Abs., 104 (11), 88398k/1986.

Compounds of general formula (II) can be prepared, for example, in the following way:

1) when A is an —$NR^4$—CO— radical, 1.1) a compound of the general formula (III) is reacted with a compound of the general formula:

Z—CO—B—OH  (X)

in which R, n, $R^4$, B and Z have the above-given meanings, or 1.2) a compound of general formula (III) is reacted with a compound of the general formula:

Z—CO—B—O—W  (XI)

in which R, n, $R^4$, B and Z have the above-given meanings and W is a protective group, and the protective group W is subsequently split off, or 1.3) a compound of the general formula (III) is reacted with a lactone of the general formula:

CO—B—O  (XII)

in which R, n, $R^4$ and B have the above-given meanings, or 1.4) a compound of the general formula:

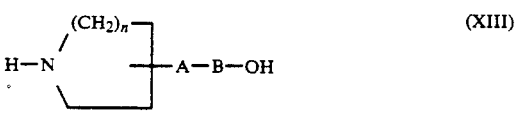
H—N$\diagup^{(CH_2)_n}_{\diagdown}$—A—B—OH  (XIII)

is reacted with a compound of general formula (VIII), in which n, A, B, R and Z have the above-given meanings, or 1.5) when R contains an $R^1R^2N$— radical, a compound of the general formula (XIII) is reacted with a compound of the general formula:

V—R''—Z  (XIV)

in which n, A, B and Z have the above-given meanings, R'' is a ($C_1$-$C_8$)-alkylene, ($C_1$-$C_8$)alkylene-CO— or ($C_1$-$C_8$)-alkylene-CO—$NR^3$—($C_1$-$C_8$)-alkylene radical and V is a protective group which can be converted into an $R^1R^2N$— radical, or 2) when A is a —CO—$NR_4$ radical, 2.1) a compound of the general formula (V) is reacted with a compound of the general formula:

$HNR^4$—B—OH  (XV)

in which R, n, Z, R⁴ and B have the above-given meanings, or 2.2) a compound of the general formula (V) is reacted with a compound of the general formula:

$$HNR^4-B-O-W \qquad (XVI)$$

in which R, n, Z, R⁴, B and W have the above-given meanings, and subsequently the protective group W is split off.

The nitrate ester-forming reaction of the compounds of the general formulae (II), (X), (XIII) or (XV) can be carried out by reacting a compound of general formula (II), (X), (XIII) or (XV) with a nitrate ester-forming reagent, for example fuming nitric acid, a mixture of fuming nitric acid and acetic anhydride or a mixture of fuming nitric acid and concentrated sulphuric acid at a low temperature in the presence or absence of an inert solvent. The reaction temperature is from ambient temperature to −60° C. and preferably from −10° C. to −30° C. The mole ratio of the reaction components is from 1 to 10.

Alternatively, the nitrate ester-forming reaction can be carried out by selectively replacing the aliphatic hydroxyl group in a compound of general formula (II), (X), (XIII) or (XV) by a halogen atom or an alkyl- or aryl-sulphonic acid ester group and subsequently reacting the reaction product with, for example, silver nitrate or tetrabutylammonium nitrate in the presence or absence of a solvent at a temperature of from ambient temperature and 100° C. The mole ratio of the reaction between the halogen compound and silver nitrate can be from 1 to 10.

The nucleofugic group Z can be, for example, an alcoholate, tosylate, mesylate, halide or alkyl carboxylate. Therefore, the corresponding activated carboxylic acids (IV), (V), (VIII), (X), (XI) or (XIV) are present in the form of esters, carboxylic acid halides or anhydrides.

The activation of the carboxylic acids can, however, also take place by means of activating reagents, for example, N,N'-carbonyldiimidazole, N,N'-dicyclohexylcarbodiimide, 1-ethyl-3-(3-dimethylaminopropyl)-carbodiimide, 1-alkyl-2-halopyridinium salts and the like. When the compounds of general formulae (VIII) or (XIV) are not carboxylic acid derivatives, these can be present as halides, tosylates or mesylates. The molar ratio between the reaction components can be from 1 to 100.

As protective group W, there is preponderantly used the acetyl radical. However, in addition thereto, there can also be used a tetrahydropyranyl, benzoyl or benzyl radical. The splitting off of the protective group can take place in the usual manner in acidic or basic, aqueous or alcoholic solution.

As protective group V, there can be used, for example, the $NO_2$ group, the azido group, the benzyloxycarbonyl group or an amine group protected by one or two benzyl radicals. Furthermore, V can be a nucleofuge group, for example, halide, mesylate or tosylate, which are reacted with benzyl group-protected primary and secondary amines or the amines of the general formula $R^1R^2NH$. For the reduction of the $NO_2$ group or of the azido group, there can be used numerous processes, for example zinc in hydrochloric acid, iron in hydrochloric acid, lithium aluminium hydride in ethers, sodium borohydride in alcohols, ammonium formate in the presence of nobel metal catalysts, such as palladium or platinum, inorganic sulphides, such as sodium hydrogen sulphide, ammonium sulphide or sodium hydrosulphite in aqueous and/or alcoholic solution or hydrogenolytically with catalysts, for example platinum dioxide, palladium or Raney nickel, preferably in an alcoholic solvent, for example methanol or ethanol, at a pressure of from 1 to 200 bar. The temperature can be from −20° to +200° C. and preferably between ambient temperature and 100° C. The reaction of amines with halides, mesylates or tosylates takes place in the presence or absence of a solvent at a temperature of from 0° to 150° C. and preferably of from 20° to 80° C. As solvent, there can be used, for example, methanol, ethanol, propanol, isopropanol, ethers, such as diethyl ether, diisopropyl ether, tert.-butyl methyl ether or tetrahydrofuran, or aromatic solvents, for example, toluene or xylene. The molar ratio of the reaction components is not critical. There can be used ratios of from 1 to 100. The reactions can possibly also be carried out under an elevated pressure. The splitting off of benzyl protective groups takes place hydrogenolytically in the presence of an organic solvent and/or water, as well as of palladium of carbon as catalyst. The temperature can be from ambient temperature to 250° C. and preferably from ambient temperature and 60° C. and the hydrogen pressure can be from 1 to 300 bar and preferably from 1 to 5 bar.

The compounds of general formulae (I) and (II) according to the present invention can possess asymmetric carbon atoms. Therefore, the present invention also includes all possible racemates and diastereomeric mixtures, as well as all optically-active forms of the compounds according to the present invention of general formula (I) and (II).

For the conversion of compounds of general formula (I) into the pharmacologically acceptable salts thereof, these are reacted, preferably in an organic solvent, with an equivalent amount of an inorganic or organic acid, for example hydrochloric acid, hydrobromic acid, nitric acid, phosphoric acid, sulphuric acid, formic acid, acetic acid, propionic acid, oxalic acid, fumaric acid, maleic acid, succinic acid, adipic acid, benzoic acid, salicylic acid, o-acetoxybenzoic acid, cinnamic acid, naphthoic acid, mandelic acid, citric acid, malic acid, tartaric acid, aspartic acid, glutamic acid, methanesulphonic acid, p-toluenesulphonic acid or cyclohexylsulphamic acid.

The new compounds of general formula (I) according to the present invention can be administered enterally or parenterally in liquid or solid form as such or in the form of their salts. As injection medium, it is preferred to use water which contains additives usual in the case of injection solutions, such as stabilising agents, solubilising agents or buffers. Such additives include, for example, tartrate and citrate buffers, ethanol, complex formers (such as ethylenediamine-tetraacetic acid and the non-toxic salts thereof), high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening materials.

Besides the compounds described in the following Examples, the following compounds, as well as the corresponding hydroxy compounds which are not nitrated (intermediates), are preferred according to the present invention:

N-(3-nitroxypropyl)-pyrrolidine-2-carboxylic acid amide
1-methyl-N-(2-methyl-1-nitroxyprop-2-yl)-piperidine-2-carboxylic acid amide
1-methyl-N-(3-nitroxypropyl)-piperidine-2-carboxylic acid amide
1-methyl-N-(2-methyl-1-nitroxyprop-2-yl)-piperidine-2-carboxylic acid amide
1-methyl-N-(3-nitroxypropyl)-piperidine-3-carboxylic acid amide
1-methyl-N-(4-nitroxy-2-methylbut-2-yl)-piperidine-3-carboxylic acid amide
1-methyl-N-(1-nitroxy-2-methylprop-2-yl)-piperidine-4-carboxylic acid amide
1-methyl-N-(1-nitroxy-3-methyl-but-3-yl)-piperidine-4-carboxylic acid amide
2-nitroxy-N-(piperidin-4-yl)-propionic acid amide
2-methyl-2-nitroxy-N-(piperidin-4-yl)-propionic acid amide
2,2-dimethyl-3-nitroxy-N-(piperidin-4-yl)propionic acid amide
2-nitroxy-N-(1-methylpiperidin-4-yl)-propionic acid amide
2-methyl-2-nitroxy-N-(1-methylpiperidin-4-yl)-propionic acid amide
trans-N-(2-nitroxycyclohexyl)-pyrrolidine-2-carboxylic acid amide
trans-N-(4-nitroxycyclohexyl)-pyrrolidine-2-carboxylic acid amide
trans-1-methyl-N-(4-nitroxycyclohexyl)-piperidine-2-carboxylic acid amide
trans-1-methyl-N-(4-nitroxycyclohexyl)-piperidine-3-carboxylic acid amide
trans-1-methyl-N-(2-nitroxycyclohexyl)-piperidine-4-carboxylic acid amide
trans-1-methyl-N-(4-nitroxycyclohexyl)-piperidine-4-carboxylic acid amide
cis-1-methyl-N-(4-nitroxycyclohexyl)-piperidine-4-carboxylic acid amide
trans-1-methyl-N-(4-nitroxycyclohexylmethyl)-piperidine-4-carboxylic acid amide
cis-1-methyl-N-(4-nitroxycyclohexylmethyl)-piperidine-4-carboxylic acid amide
trans-1-methyl-N-(4-nitroxymethylcyclohexyl)-piperidine-4-carboxylic acid amide
cis-1-methyl-N-(4-nitroxymethylcyclohexyl)-piperidine-4-carboxylic acid amide
trans-4-nitroxy-N-(piperidin-4-yl)-cyclohexanecarboxylic acid amide
cis-4-nitroxy-N-(piperidin-4-yl)-cyclohexanecarboxylic acid amide
cis-2-(4-nitroxycyclohexyl)-N-(piperidin-4-yl)-acetamide
cis-4-nitroxy-N-(1-methylpiperidin-4-yl)-cyclohexanecarboxylic acid amide
cis-2-(4-nitroxycyclohexyl)-N-(1-methylpiperidin-4-yl)-acetamide
2-aminoacetic acid 4-nitroxymethylpiperidide
2-aminoacetic acid 4-(2-nitroxyethyl)-piperidide
2-aminoacetic acid 4-(1-nitroxyethyl)-piperidide
2-dimethylaminoacetic acid 4-nitroxymethylpiperidide
2-dimethylaminoacetic acid 4-(2-nitroxyethyl)-piperidide
2-dimethylaminoacetic acid 4-(1-nitroxyethyl)-piperidide
L-2-aminopropionic acid 4-nitroxypiperidide
L-2-aminopropionic acid 4-nitroxymethylpiperidide
L-2-aminopropionic acid 4-(2-nitroxyethyl)-piperidide
3-amino-3-methylbutyric acid 4-nitroxypiperidide
3-dimethylaminopropionic acid 4-nitroxymethylpiperidide
3-dimethylaminopropionic acid 4-(2-nitroxyethyl)-piperidide
3-amino-3-methylbutyric acid 4-nitroxymethylpiperidide
3-amino-3-methylbutyric acid 4-(2-nitroxyethyl)-piperidide
1-methylpiperidine-2-carboxylic acid 4-nitroxymethylpiperidide
1-methylpiperidine-3-carboxylic acid 4-nitroxymethylpiperidide
piperidine-4-carboxylic acid 4-nitroxymethylpiperidide
piperidine-4-carboxylic acid 4-(2-nitroxyethyl)-piperidide
1-methylpiperidine-4-carboxylic acid 4-nitroxymethylpiperidide
1-methylpiperidine-4-carboxylic acid 4-(2-nitroxyethyl)-piperidide
4-nitroxy-1-(2-propyl)-piperidine The following Examples are given for the purpose of illustrating the present invention:

EXAMPLE 1

1-Methyl-N-(2-nitroxyethyl)-piperidine-4-carboxylic acid amide fumarate 10.2 g. 1-Methyl-N-(2-hydroxyethyl)-piperidine-4-carboxylic acid amide are introduced, while stirring at −10° to −5° C., into 23 ml. 100% nitric acid. The reaction mixture is further stirred for 2 hours at 5° C., 300 ml. methylene chloride are then added thereto followed by neutralisation with 76 g. potassium carbonate sesquihydrate. The reaction mixture is stirred for 18 hours at ambient temperature, filtered with suction and the filtrate is evaporated in a vacuum at 20° C. The residue (11.2 g.) is dissolved in ethanol. By the addition of 2.8 g. fumaric acid, there are obtained 5.9 g. of the fumarate of the title compound, i.e. 47% of theory; m.p. 123°–127° C.

The following compounds are obtained in an analogous manner:

1) 1-methyl-N-(3-nitroxypropyl)-piperidine-4-carboxylic acid amide fumarate from 1-methyl-N-(3-hydroxypropyl)-piperidine-4-carboxylic acid amide oxalate; yield 31% of theory; solvent: ethanol; m.p. 111°–113° C.

2) N-(1-methylpiperidin-4-yl)-4-nitroxybutyric acid amide fumarate from N-(1-methylpiperidin-4-yl)-4-hydroxybutyric acid amide oxalate; yield 70% of theory; solvent: ethyl acetate; m.p. 120°–125° C.

3) trans-M-(1-methylpiperidin-4-yl)-4-nitroxycyclohexanecarboxylic acid amide from trans-N-(1-methylpiperidin-4-yl)-4-hydroxycyclohexanecarboxylic acid amide oxalate; yield 65% of theory; solvent: dichloromethane; m.p. 181°–183° C.

4) 4-nitroxypiperidine fumarate from 4-hydroxypiperidine oxalate; yield 39% of theory; solvent: ethyl acetate; m.p. 180°–185° C.

5) 2-aminoacetic acid 4-nitroxypiperidide fumarate from 2-aminoacetic acid 4-hydroxypiperidide oxalate; yield 73% of theoryl solvent: ethyl acetate; m.p. 112°–115° C.

6) 2-dimethylaminoacetic acid 4-nitroxypiperidine oxalate from 2-dimethylaminoacetic acid 4-hydroxypiperidide oxalate; yield 61% of theory; solvent isopropanol; m.p. 160°–162° C.

7) 2-amino-2-methylpropionic acid 4-nitroxypiperidide fumarate from 2-amino-2-methylpropionic acid 4-hydroxypiperidide oxalate; yield 48% of theory; solvent: ethanol; m.p. 185° C.

8) 2-amino-2-methylpropionic acid 4-nitroxymethylpiperidide fumarate from 2-amino-2-methylpropionic acid 4-hydroxymethylpiperidide oxalate; yield 50% of theory; solvent: ethanol; m.p. 103°–105° C.

9) 2-amino-2-methylpropionic acid 4-(2-nitroxyethyl)-piperidide fumarate from 2-amino-2-methylpropionic acid 4-(2-hydroxyethyl)-piperidide oxalate; yield 53% of theory; solvent: ethanol; m.p. 155°–157° C.

10) 3-aminopropionic acid 4-nitroxypiperidide fumarate from 3-aminopropionic acid 4-hydroxypiperidide oxalate; yield 64% of theory; solvent: ethanol; m.p. 141°–142° C.

11) 3-aminopropionic acid 4-nitroxymethylpiperidide fumarate from 3-aminopropionic acid 4-hydroxymethylpiperidide oxalate; yield 64% of theory; solvent: ethanol; m.p. 141°–142° C.

12) 3-dimethylaminopropionic acid 4-nitroxypiperidide oxalate from 3-dimethylaminopropionic acid 4-hydroxypiperidide oxalate; yield 29% of theory; solvent: isopropanol; m.p. 130°–132° C.

13) 4-amino-4-methylvaleric acid 4-nitroxypiperidide fumarate from 4-amino-4-methylvaleric acid 4-hydroxypiperidide oxalate; yield 53% of theory; solvent: ethyl acetate; m.p. 263°–265° C.

14) 4-amino-4-methylvaleric acid 4-nitroxymethylpiperidide fumarate from 4-amino-4-methylvaleric acid 4-hydroxymethylpiperidide oxalate; yield 28% of theory; solvent: ethyl acetate/acetone; m.p. 142°–145° C.

15) 1-(2-aminoethyl)-4-nitroxypiperidine fumarate from 1-(2-aminoethyl)-4-hydroxypiperidine oxalate; yield 60% of theory; solvent: ethanol; m.p. 167° C.

16) 1-(2-aminoethyl)-4-nitroxymethylpiperidine difumarate from 1-(2-aminoethyl)-4-hydroxymethylpiperidine oxalate; yield 35% of theory; solvent: ethanol; m.p. 150°–153° C.

17) 1-(3-aminopropyl)-4-nitroxypiperidine fumarate from 1-(3-aminopropyl)-4-hydroxypiperidine oxalate; yield 35% of theory; solvent: ethanol; m.p. 150°–154° C.

18) 1-(3-aminopropyl)-4-nitroxymethylpiperidine fumarate from 1-(3-aminopropyl)-4-hydroxymethylpiperidine oxalate; yield 40% of theory; solvent: ethanol; m.p. 128°–130° C.

19) 2,2-dimethyl-3-nitroxy-N-(1-methylpiperidin-4-yl)-propionic acid amide fumarate from 2,2-dimethyl-3-hydroxy-N-(1-methylpiperidin-4-yl)-propionic acid amide oxalate; yield 20% of theory; solvent: ethanol; m.p. 180°–183° C.

20) 5-nitroxy-N-(1-methylpiperidin-4-yl)-valeric acid amide fumarate from 5-hydroxy-N-(1-methylpiperidin-4-yl)-valeric acid amide oxalate; yield 15% of theory; solvent: ethanol; m.p. 102°–106° C.

21) 1-(2-aminoethyl)-4-(2-nitroxyethyl)-piperidine difumarate from 1-(2-aminoethyl)-4-(2-hydroxyethyl)-piperidine oxalate; yield 20% of theory; solvent: ethanol; m.p. 140°–142° C.

22) (S)-N-(2-nitroxyethyl)-pyrrolidine-2-carboxylic acid amide fumarate from (S)-N-(2-hydroxyethyl)-pyrrolidine-2-carboxylic acid amide oxalate; yield 25% of theory; solvent: ethanol; m.p. 125°–126° C.

23) 1-methyl-N-(2-nitroxyethyl)-piperidine-2-carboxylic acid amide fumarate from 1-methyl-N-(2-hydroxyethyl)-piperidine-2-carboxylic acid amide; yield 45% of theory; solvent: ethanol; m.p. 120°–122° C.

24) 1-methyl-N-(2-nitroxyethyl)-piperidine-3-carboxylic acid amide fumarate from 1-methyl-N-(2-hydroxyethyl)-piperidine-3-carboxylic acid amide oxalate; yield 56% of theory; solvent: ethanol; m.p. 99°–102° C.

25) 3-aminopropionic acid 4-(2-nitroxyethyl)-piperidide fumarate from 3-aminopropionic acid 4-(2-hydroxyethyl)-piperidide oxalate; yield 11% of theory; solvent: ethanol; m.p. 128°–130° C.

26) 4-amino-4-methylvaleric acid 4-(2-nitroxyethyl)-piperidide fumarate from 4-amino-4-methylvaleric acid 4-(2-hydroxyethyl)-piperidide; yield 70% of theory; solvent: ethanol; m.p. 150°–152° C.

27) piperidine-4-carboxylic acid 4-nitroxypiperidide fumarate from piperidine-4-carboxylic acid 4-hydroxypiperidide; yield 60% of theory; solvent: ethanol; m.p. 164°–168° C.

28) 4-(2-nitroxyethyl)-piperidine cyclamate from 4-(2-hydroxyethyl)-piperidine oxalate; yield 60% of theory; solvent: ethyl acetate; m.p. 82°–83° C.

29) 2-(2-nitroxyethyl)-piperidine cyclamate from 2-(2-hydroxyethyl)-piperidine oxalate; yield 90% of theory; solvent: ethyl acetate; m.p. 131°–133° C.

30) 4-nitroxybutyric acid N-(piperidin-4-yl)-amide cyclamate from 4-hydroxybutyric acid N-(piperidin-4-yl)-amide; yield 15% of theory; solvent: ethyl acetate/ethanol; m.p. 113°–115° C.

31) 2-dimethylaminoacetic acid 4-nitroxymethylpiperidide fumarate from 2-dimethylaminoacetic acid 4-hydroxymethylpiperidide oxalate; yield 73% of theory; solvent: ethanol; m.p. 133°–135° C.

32) trans-4-nitroxycyclohexanecarboxylic acid N-(piperidin-4-yl)-amide cyclamate from trans-4-hydroxycyclohexanecarboxylic acid N-(piperidin-4-yl)amide; yield 27% of theory; solvent: diethyl ether; m.p. 153°–155° C.

33) 1-(n-butyl)-N-(2-nitroxyethyl)-piperidine-4-carboxylic acid amide fumarate from 1-(n-butyl)-N-(2-hydroxyethyl)-piperidine-4-carboxylic acid amide; yield 63% of theory; solvent: ethanol/diethyl ether; m.p. 109°–110° C.

34) 1-(2-methyl-1-propyl)-N-(2-nitroxyethyl)-piperidine-4-carboxylic acid amide fumarate from 1-(2-methyl-1-propyl)-N-(2-hydroxyethyl)-piperidine-4-carboxylic acid amide; yield 55% of theory; solvent: ethanol; m.p. 119°–121° C.

35) 1-methylpiperidine-4-carboxylic acid 4-nitroxypiperidide fumarate from 1-methyl-piperidine-4-carboxylic acid 4-hydroxypiperidine; yield 74% of theory; solvent: ethanol; m.p. 173°–175° C.

EXAMPLE 2

4-Nitroxymethylpiperidine nitrate 5.8 g. 4-Hydroxymethylpiperidine are dissolved in 100 ml. acetonitrile and cooled to −25° C. By the addition of 3.1 ml. 100% nitric acid, the base is converted into the nitric acid salt. To this solution is added a freshly prepared acetyl nitrate solution (prepared from 9.5 ml. acetic anhydride and 4.2 ml. 100% nitric acid in 40 ml. acetonitrile at −25° C.) and the reaction mixture then stirred for 3 hours at this temperature. The reaction solution is diluted with 300 ml. diisopropyl ether. The crystals obtained are filtered off with suction and washed with diethyl ether. There are obtained 9.5 g. (82% of theory) of the nitrate of the title compound; m.p. 64°–65° C.

EXAMPLE 3

1-Isopropylaminocarbonyl-4-nitroxypiperidine 7 g. 4-Nitroxypiperidine are dissolved in 25 ml. ethyl acetate and mixed with 5.2 ml. isopropyl isocyanate while cooling with ice water to 0° to 5° C. The reaction mixture is stirred for 2 hours at 10° C. and then evaporated in a vacuum. The residue is taken up in diethyl ether and the precipitated crystals are filtered off with suction. There are obtained 6.6 g. of the title compound; m.p. 93°–95° C., 60% of theory.

EXAMPLE 4

1-Aminocarbonyl-4-nitroxypiperidine 7.1 g. 4-Nitroxypiperidine are dissolved in 60 ml. water and 30 ml. methanol and mixed with 16.2 g. potassium cyanate. After the dropwise addition of 12 ml. glacial acetic acid, stirring is continued at ambient temperature for 4 hours. The inorganic salts are precipitated out by the addition of 100 ml. ethyl acetate. After suction filtration, the aqueous phase is separated off and the organic phase is dried with anhydrous sodium sulphate. After suction filtration, the filtrate is evaporated in a vacuum. The residue is triturated with diethyl ether and the crystals are filtered off with suction. There are obtained 8.3 g. of the title compound, i.e. 89% of theory; m.p. 110°–111° C.

The following compounds are prepared in an analogous manner:
1) 1-aminocarbonyl-4-nitroxymethylpiperidine from 4-nitroxymethylpiperidine and potassium cyanate; yield 55% of theory; solvent: diethyl ether; m.p. 95°–97° C.
2) 1-aminocarbonyl-4-(2-nitroxyethyl)-piperidine from 4-(2-nitroxyethyl)-piperidine and potassium cyanate; yield 75% of theory; solvent: diethyl ether; m.p. 74°–76° C.
3) N-(1-aminocarbonylpiperidin-4-yl)-4-nitroxybutyric acid amide from 4-nitroxybutyric acid piperidin-4-ylamide; yield: 25% of theory; solvent: ethanol; m.p. 106°–107° C.
4) N-(1-aminocarbonylpiperidin-4-yl)-2,2-dimethyl-3-nitroxypropionic acid amide from 2,2-dimethyl-3-nitroxypropionic acid piperidin-4-ylamide; yield 83% of theory; solvent: ethyl acetate; m.p. 142°–143° C.
5) N-(1-aminocarbonylpiperidin-4-yl)-5-nitroxyvaleric acid amide from 5-nitroxyvaleric acid piperidin-4-ylamide; yield 49% of theory; solvent: ethyl acetate/diethyl ether; m.p. 117°–118° C.
6) trans-N-(1-aminocarbonylpiperidin-4-yl)-4-nitroxycyclohexanecarboxylic acid amide from trans-4-nitroxycyclohexanecarboxylic acid piperidin-4-ylamide; yield 25% of theory; solvent: ethanol; m.p. 187°–188° C.

EXAMPLE 5

1-(2-aminocarbonylaminoethyl)-4-nitroxypiperidine 1.53 g. 1-(2-aminoethyl)-4-nitroxypiperidine fumarate are dissolved in 15 ml. methanol and 5 ml. water. 1.62 g. Potassium cyanate is added thereto and the reaction mixture is stirred overnight at ambient temperature. A pH value of 10 is adjusted by the addition of potassium carbonate. The reaction mixture is extracted with ethyl acetate and the extracts are dried with anhydrous sodium sulphate. After evaporation and trituration of the residue with diethyl ether, the resultant crystals are filtered off with suction. There is obtained 1 g. of the title compound, i.e. 86% of theory; m.p. 114°–116° C.

EXAMPLE 6

1-Ethyl-4-nitroxypiperidine fumarate 6.9 g. 4-Nitroxypiperidine are dissolved in 50 ml. acetone, mixed with 13.8 g. potassium carbonate and 6.1 ml. ethyl iodide and stirred for 18 hours at ambient temperature. After filtering with suction, the filtrate is evaporated, the residue is dissolved in ethyl acetate and extracted twice with aqueous sodium chloride solution. The organic phase is dried with anhydrous sodium sulphate. The crude product (8.2 g.) remaining after suction filtration and evaporation is converted into the fumarate by dissolving in ethanol and adding 2.7 g. fumaric acid. After filtering off with suction, there are obtained 2.6 g. of the fumarate of the title compound, i.e. 23% of theory; m.p. 131°–134° C.

The following compounds are prepared in an analogous manner:
1) 4-nitroxy-1-propylpiperidine fumarate from 4-nitroxypiperidine and n-propyl iodide; yield 30% of theory; solvent: ethanol; m.p. 122°–125° C.
2) 4-nitroxybutyric acid N-(1-propylpiperidin-4-yl)-amide fumarate from 4-nitroxybutyric acid N-(piperidin-4-yl)-amide and n-propyl iodide; yield 10% of theory; solvent: ethyl acetate; m.p. 100°–102° C.
3) 4-nitroxy-1-hexylpiperidine fumarate from 4-nitroxypiperidine and n-hexyl bromide; yield 50% of theory; solvent: ethanol; m.p. 102°–103° C.

EXAMPLE 7

1-(2-Hydroxypropyl)-4-nitroxypiperidine hemifumarate 6.9 g. 4-Nitroxypiperidine are dissolved in 25 ml. ethanol, mixed with 10.5 ml. 1,2-epoxypropane and stirred for 2 days at ambient temperature. The residue (11.4 g.) obtained after evaporation is dissolved in 10 ml. ethanol and mixed with 3.5 g. fumaric acid. The precipitate obtained is filtered off with suction and there are obtained 6.3 g. of the hemifumarate of the title compound, i.e. 50% of theory; m.p. 135°–138° C.

EXAMPLE 8

1-Methyl-4-(2-nitroxyethyl)-piperidine fumarate

To 100 ml. of a 1N solution of monosodium dihydrogen phosphate are added 3.4 g. (0.02 mole) 4-(2-nitroxyethyl)-piperidine in 10 ml. dioxan. While cooling and stirring, there are now added dropwise at +10° C., 10 ml. of a 37% solution of formaldehyde in the course of 10 minutes. After stirring overnight at ambient temperature, the reaction mixture is rendered alkaline with potassium carbonate and extracted with ethyl acetate. The organic phase is dried with anhydrous sodium sulphate and distilled in a vacuum. The remaining oil is dissolved in ethanol and converted into the salt by the addition of 1.2 g. fumaric acid. After filtering off with suction, there are obtained 2 g. of the fumarate of the title compound, i.e. 33% of theory; m.p. 105°–107° C.

EXAMPLE 9 a) 3-Aminopropionic acid 4-hydroxypiperidide hemioxalate 113 g. Ethyl 2-cyanoacetate are dissolved in 1 liter methylene chloride and mixed with 75.1 g. 4-hydroxypiperidine. After stirring for 3 days at ambient temperature, it is distilled off in a vacuum. There are obtained 153 g. of crude product of 2-cyanoacetic acid 4-hydroxypiperidide, i.e. about 100% of theory.

61 g. of this product are dissolved in 300 ml. methanol, mixed with 300 ml. liquid ammonia and hydrogenated in the presence of 20 g. Raney nickel at 100 bar hydrogen pressure and ambient temperature. After filtering off the catalyst with suction, the solvent is distilled off in a vacuum, the residue is dissolved in 400 ml. ethanol and mixed with 19.4 g. oxalic acid in 200 ml. ethanol. After standing overnight, it is filtered off with suction. There are obtained 64.2 g. of the hemioxalate of the title compound, i.e. 75% of theory; m.p. 170°–172° C.

b) 4-Amino-4-methylvaleric acid 4-hydroxypiperidide oxalate

To a solution of 180 ml. 2-nitropropane in 25.8 ml. 35% benzyltrimethylammonium hydroxide solution and 100 ml. isobutanol is added dropwise at about 35° C. 181 ml. methyl acrylate. The reaction mixture is allowed to cool and extracted with methylene chloride and water. The organic phase is dried with anhydrous sodium sulphate and evaporated. The residue is fractionally distilled (b.p.$_3$=84°–87° C.). There are obtained 285 g. (82% of theory) methyl 4-methyl-4-nitrovalerate.

175 g. of this product are mixed with 500 ml. 2N aqueous sodium hydroxide solution and stirred for 4 hours at ambient temperature. The water is distilled off and the solid residue is dried in a vacuum drying cabinet. There are obtained 183.1 g. (100% of theory) of the sodium salt of 4-methyl-4-nitrovaleric acid.

To a suspension of this salt in 1 liter methylene chloride, there are added, while cooling, 208.2 g. phosphorus pentachloride. The reaction mixture is stirred for 15 hours at ambient temperature, filtered off with suction from insolubles and the filtrate is evaporated. There are obtained 153 g. (85% of theory) of 4-methyl-4-nitrovaleric acid chloride in the form of an oil.

To a solution of 4-hydroxypiperidine in 340 ml. acetone, 35.7 g. sodium acetate and 218 ml. water is added dropwise at 0° to 5° C. a solution of 39.1 g. 4-methyl-4-nitrovaleric acid chloride in 108 ml. acetone. The reaction mixture is stirred for 15 hours at ambient temperature, the solvent is then distilled off, the residue is taken up in 600 ml. methylene chloride and washed twice with, in each case, 30 ml. saturated aqueous sodium chloride solution. The organic phase is dried and evaporated. There are obtained 57.9 g. of crude 4-methyl-4-nitrovaleric acid 4-hydroxypiperidide.

This crude product is dissolved in 600 ml. ethanol, mixed in an autoclave with 600 ml. ammonia and 8 g. Raney nickel and hydrogenated for 10 hours at 40° C. and 80 bar hydrogen pressure. The pressure is released, the reaction mixture is evaporated and the solid residue is triturated with ethyl acetate. There are obtained 33.8 g. of a solid material. This is dissolved in isopropanol and mixed at an elevated temperature with 14.2 g. oxalic acid. The reaction mixture is allowed to cool and filtered off with suction. There are obtained 39.5 g. (55% of theory) of the title compound; m.p. 106°–109° C.

c) 5-Hydroxy-N-(1-methylpiperidin-4-yl)-valeric acid amide oxalate 5.3 g. (0.05 mole) 4-amino-1-methylpiperidine are heated with 5.4 ml. (0.06 mole) γ-valerolactone for 48 hours at 90° C. The reaction mixture is dissolved in 50 ml. water and shaken up with methylene chloride. The aqueous phase is rendered alkaline with potassium carbonate and extracted with n-butanol. The crude base is dissolved in ethanol, 3 g. oxalic acid are added thereto, insolubles are filtered off and the filtrate is distilled off. There are obtained 8.5 g. of the oxalate of the title compound in the form of a viscous, semi-solid product. Yield 56% of theory.

In an analogous manner, from β-butyrolactone, there is obtained:

c1) 4-hydroxy-N-(1-methylpiperidin-4-yl)-butyric acid amide oxalate; yield 35% of theory; m.p. 40° C. (sinters) (recrystallised from diethyl ether).

d) 1-Methyl-N-(2-hydroxyethyl)-piperidine-4-carboxylic acid amide 17.1 g. (0.1 mole) 1-Methylpiperidine-4-carboxylic acid ethyl ester (literature: J.A.C.S., 74, 3831/1952). are heated to 60° C. for 48 hours with 9 ml. (0.15 mole) 2-hydroxyethylamine and purified over a silica gel column with methylene chloride/methanol (9:1 v/v). There are obtained 9.5 g. of base in the form of a viscous oil. Yield 52% of theory.

With 3-hydroxypropylamine, there is obtained analogously:

d1) 1-methyl-N-(3-hydroxypropyl)-piperidine-4-carboxylic acid amide; yield 80% of theory; m.p. 40° C.

e) 2-Amino-2-methylpropionic acid 4-hydroxypiperidide oxalate 3.8 g. (18 mmole) 2-Azido-2-methylpropionic acid 4-hydroxypiperidide are dissolved in 10 ml. methanol and hydrogenated over Raney nickel at ambient temperature and 1 bar hydrogen pressure. After filtering off with suction and evaporation of the filtrate, the residue is reacted in ethanol with oxalic acid. There are obtained 3.0 g. of the oxalate of the title compound; m.p. 197° C. Yield 74% of theory.

The following compounds are prepared in an analogous manner:

e1) 2-amino-2-methylpropionic acid 4-hydroxymethylpiperidide oxalate; yield 65% of theory; m.p. 177°–178° C., after recrystallisation from ethanol.

e2) 2-amino-2-methylpropionic acid 4-hydroxyethylpiperidide oxalate; yield 63% of theory; m.p. 179° C., after recrystallisation from ethanol.

f) 2-Azido-2-methylpropionic acid 4-hydroxymethylpiperidide 15 g. (0.13 mole) 4-Hydroxymethylpiperidine are dissolved in 130 ml. water and 30 ml. dioxan and 19.4 g. (0.13 mole) 2-azido-2-methylpropionic acid chloride (according to analogous literature: J.A.C.S., 77, 112/1955) added dropwise thereto. The pH of the solution is kept at 12 to 12.5 by the simultaneous dropwise addition of 2N aqueous sodium hydroxide solution. After ending of the reaction, the reaction mixture is extracted with diethyl ether. After drying with anhydrous sodium sulphate and evaporating, there are obtained 17.8 g. of crude oil, i.e. 60% of theory, which can be used in the next step without further purification.

The following compounds are prepared analogously, with 4-hydroxyethylpiperidine:

f1) 2-azido-2-methylpropionic acid 4-hydroxyethylpiperidide; oil; yield 56% of theory.

f2) with 4-hydroxypiperidine: 2-azido-2-methylpropionic acid 4-hydroxypiperidide; oil; yield 60% of theory.

TEST PROTOCOL

The compounds of the present invention have nitrate-like properties with a especially long duration of action and are therefore preferably useful in the treatment of anti-angina diseases, i.e. heart diseases which are characterized by pain attacks whereby the oxygen requirement of the heart has not sufficient security. Presently, there are used for the treatment of coronary heart diseases nitrate compounds, such as nitroglycerol, isosorbitdinitrate (ISDN), isosorbitmononitrate (ISMO) as well as β-blocking compounds, such as propranolol. These hitherto known compounds have however a short duration of action due to the relatively fast denitration velocity (hydrodysis of the nitrato group).

METHOD

To show denitration properties (which constitutes the working principle of all nitrates; see U. Abshagen in Handbook of Experimental Pharmacology, Vol. 76, 1985, Chapter 10.) the denitration rate was evaluated in relation to that of the known isosorbide dinitrate metabolite isosorbide-5-mononitrate ($V_{rel}$). To that end, rats were killed under narcosis and their livers reperfused 4 min with a corresponding concentrated equimolar ($5 \times 10^{-5}$ M/l) solution of isosorbide-5-mononitrate and the substances to be tested respectively (a blood sediment solution was pumped through the liver vessels) and the freed amount in $NO_2$ determined in the perfusate (outflowing fluid). To have comparable conditions, the perfusion with isosorbide-5-mononitrate (standard substance) was administered as control at the second time as if it were an unknown substance (in this way a liver performance change under the test conditions can be recognized and accordingly allowed for).

The following table gives the results for some selected compounds:

TABLE

| compound of example | liver perfusion (relative denitration rate) $V_{rel}$ |
|---|---|
| ISMO | 0.95 |
| 1.2 | 0.49 |
| 1.5 | 0.44 |
| 1.15 | 0.32 |
| 1.28 | 0.44 |

The compounds according to the present invention seem to be particularly useful for the therapy because $V_{rel}$ has a sufficiently long duration of action at a comparatively low concentration (i.e. low dosage to be administered).

What is claimed is:

1. A compound of the formula:

$$R-N\begin{Bmatrix}(CH_2)_n\\ \\ \end{Bmatrix}-A-B-ONO_2 \quad (I)$$

wherein:

n is 1 or 2,

R is a hydrogen atom or an H—($C_1$-$C_8$)-alkylene, hydroxy-($C_1$-$C_8$)-alkylene, $R^1R^2N$—($C_1$-$C_8$)-alkylene, $R^1R^2N$—($C_1$-$C_8$)-alkylene-co, $R^1R^2N$—CO—$NR^3$—($C_1$-$C_8$)-alkylene, or $R^1R^2N$—CO— radical, $R^1$ is a hydrogen atom or a straight-chained or branched, saturated or unsaturated radical containing 1 to 6 carbon atoms or a cyclic alkyl radical containing 3 to 6 carbon atoms, $R^2$ is a hydrogen atom or a straight chain or branched, saturated or unsaturated radical containing 1 to 6 carbon atoms or a cyclic alkyl radical containing 3 to 6 carbon atoms $R^3$ is a hydrogen atom or a straight chained or branched, saturated or unsaturated radical containing 1 to 6 carbon atoms, or a cyclic alkyl radical containing 3 to 6 carbon atoms, A is a valency bond or a —$NR^4$—CO— or —CO—$NR^4$— radical in which $R^4$ is a hydrogen atom or a straight chain or branched, saturated or unsaturated radical containing 1 to 6 carbon atoms or a cyclic alkyl radical containing 3 to 6 carbon atoms, and B is a straight chained or branched alkylene chain containing 1 to 8 carbon atoms, in which a —$CH_2$— group can be replaced by a cycloalkylene radical containing 3 to 6 carbon atoms, with the proviso that R cannot be a $R^1R^2N$—($C_1$-$C_8$)-alkylene-CO— or $R^1R^2N$—($C_1$-$C_8$)-alkylene radical in which $R^1$ and $R^2$ are both hydrogen atoms, or an optically-active isomer thereof or a pharmaceutically acceptable salt thereof.

2. A compound of the formula:

$$R-N\begin{Bmatrix}(CH_2)_n\\ \\ \end{Bmatrix}-A-B-ONO_2 \quad (I)$$

wherein:

n is 1 or 2,

R is a hydrogen atom or an H—($C_1$-$C_8$)-alkylene, hydroxy-($C_1$-$C_8$)-alkylene, $R^1R^2N$—($C_1$-$C_8$)-alkylene, $R^1R^2N$—($C_1$-$C_8$)-alkylene-CO, $R^1R^2N$—CO—$NR^3$—($C_1$-$C_8$)-alkylene, or $R^1R^2N$—CO— radical, $R^1$ is a hydrogen atom or a straight-chained or branched, saturated or unsaturated radical containing 1 to 6 carbon atoms or a cyclic alkyl radical containing 3 to 6 carbon atoms, $R^2$ is a hydrogen atom or a straight chain or branched, saturated or unsaturated radical containing 1 to 6 carbon atoms or a cyclic alkyl radical containing 3 to 6 carbon atoms $R^3$ is a hydrogen atom or a straight chained or branched, saturated or unsaturated radical containing 1 to 6 carbon atoms, or a cyclic alkyl radical containing 3 to 6 carbon atoms, A is a —NR$^4$—CO— or —CO—NR$^4$— radical in which R$^4$ is a hydrogen atom or a straight chain or branched, saturated or unsaturated radical containing 1 to 6 carbon atoms or a cyclic alkyl radical containing 3 to 6 carbon atoms, and B is a straight chained or branched alkylene chain containing 1 to 8 carbon atoms, in which a —CH$_2$— group can be replaced by a cycloalkylene radical containing 3 to 6 carbon atoms, with the proviso that R cannot be a R$^1$R$^2$N—(C$_1$-C$_8$)-alkylene or R$^1$R$^2$N—(C$_1$-C$_8$)-alkylene-CO— radical in which R$^1$ and R$^2$ are both hydrogen atoms, or an optically-active isomer thereof; or a pharmaceutically acceptable salt thereof.

3. The compound of claim 1, wherein B is a straight or branched alkylene chain containing up to 8 carbon atoms.

4. The compound of claim 1, wherein R is methyl and B is ethylene.

5. The compound according to claim 1, which is N-(1-methylpiperidin-4-yl)-4-nitroxybutyric acid amide.

6. A pharmaceutical composition suitable for the treatment of angina, comprising a compound of the formula:

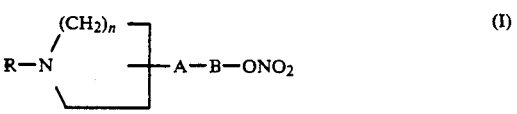

wherein:

n is 1 or 2,

R is a hydrogen atom or an H—(C$_1$-C$_8$)-alkylene, hydroxy-(C$_1$-C$_8$)-alkylene, R$^1$R$^2$N—(C$_1$-C$_8$)-alkylene, R$^1$R$^2$N—(C$_1$-C$_8$)-alkylene-CO, R$^1$R$^2$N—CO—NR$^3$—(C$_1$-C$_8$)-alkylene, or R$^1$R$^2$N—CO— radical, R$^1$ is a hydrogen atom or a straight-chained or branched, saturated or unsaturated radical containing 1 to 6 carbon atoms or a cyclic alkyl radical containing 3 to 6 carbon atoms, R$^2$ is a hydrogen atom or a straight chain or branched, saturated or unsaturated radical containing 1 to 6 carbon atoms or a cyclic alkyl radical containing 3 to 6 carbon atoms R$^3$ is a hydrogen atom or a straight chained or branched, saturated or unsaturated radical containing 1 to 6 carbon atoms, or a cyclic alkyl radical containing 3 to 6 carbon atoms, A is a valency bond or a —NR$^4$—CO— or —CO—NR$^4$— radical in which R$^4$ is a hydrogen atom or a straight chain or branched, saturated or unsaturated radical containing 1 to 6 carbon atoms, or a cyclic alkyl radical containing 3 to 6 carbon atoms, and B is a straight chained or branched alkylene chain containing 1 to 8 carbon atoms, in which a —CH$_2$— group can be replaced by a cycloalkylene radical containing 3 to 6 carbon atoms, an optically-active isomer thereof or a pharmaceutically acceptable salt thereof in an amount effective to exhibit nitrate-like activity for the prophylaxis or treatment of heart or circulatory disease, together with a pharmaceutically acceptable carrier.

7. A pharmaceutical composition according to claim 6, wherein R is a hydrogen atom; and H—(C$_1$-C$_3$)-alkylene radical; an HO—(C$_1$-C$_3$)-alkylene radical; an R$^1$R$^2$N—(C$_1$-C$_3$) alkylene radical; an R$^1$R$^2$N—(C$_1$-C$_5$)alkylenecarbonyl radical; an R$^1$R$^2$N—CO—NR$^3$—(C$_1$-C$_3$) alkylene radical; an R$^1$R$^2$N—CO— radical.

8. A pharmaceutical composition according to claim 6, wherein R$^1$ is hydrogen, methyl, ethyl or isopropyl.

9. A pharmaceutical composition according to claim 6, wherein R$^2$ is hydrogen, a C$_1$-C$_3$ radical.

10. A pharmaceutical composition according to claim 6, wherein R$^3$ is a hydrogen atom.

11. A pharmaceutical composition according to claim 6, wherein A is a valency bond, an —NH—CO— group or an —CO—NH— group.

12. A pharmaceutical composition according to claim 6, wherein B is a straight-chained or branched C$_1$-C$_5$-alkylene radical, or a cyclohexylene radical.

13. A pharmaceutical composition according to claim 6, wherein R is hydrogen or an H—(C$_1$-C$_8$)-alkylene radical.

14. A pharmaceutical composition according to claim 6 comprising the compound 4-(2-nitroxyethyl)-piperidine.

15. A pharmaceutical composition according to claim 6 wherein said disease is angina pectoris.

16. A pharmaceutical composition suitable for the treatment of angina comprising a compound as claimed in claim 1 in an amount effective to exhibit nitrate-like activity, together with a pharmaceutically acceptable carrier.

17. A method of treatment of angina in a patient in said method comprising administrating to said patient an effective amount of a compound of claim 1.

18. A method for treatment of angina which comprises administering a composition according to claim 6 to a patient in need of such treatment.

19. A method for treatment of angina which comprises administering a therapeutically effective amount of a compound according to claim 6 to a patient in need of such treatment.

* * * * *